[12] United States Patent
Hales (10) Patent No.: US 12,232,981 B2
(45) Date of Patent: Feb. 25, 2025

(54) HYDRAULIC IMPLANT INTRODUCER (71) Applicant: CARTIVA, INC., Alpharetta, GA (US)

(72) Inventor: Richard Clay Hales, Alpharetta, GA (US)

(73) Assignee: STRYKER CORPORATION, Portage, MI (US)

(*) Notice: Subject to any disclaimer, the term of this patent is extended or adjusted under 35 U.S.C. 154(b) by 629 days.

(21) Appl. No.: 17/596,395

(22) PCT Filed: Mar. 25, 2020

(86) PCT No.: PCT/US2020/024547
§ 371 (c)(1),
(2) Date: Dec. 9, 2021

(87) PCT Pub. No.: WO2021/015828
PCT Pub. Date: Jan. 28, 2021

(65) Prior Publication Data
US 2022/0233334 A1 Jul. 28, 2022

Related U.S. Application Data

(60) Provisional application No. 62/878,516, filed on Jul. 25, 2019.

(51) Int. Cl.
*A61F 2/46* (2006.01)
(52) U.S. Cl.
CPC .... *A61F 2/4618* (2013.01); *A61F 2002/4627* (2013.01)

(58) Field of Classification Search
CPC .................. A61F 2/4603; A61F 2/4618; A61F 2002/4627; A61F 2002/4625; A61F 2002/4693; A61F 2/4601; A61M 5/178
See application file for complete search history.

(56) References Cited

U.S. PATENT DOCUMENTS

| | | | |
|---|---|---|---|
| 5,167,624 A * | 12/1992 | Butler | A61B 17/1214 606/198 |
| 5,258,042 A | 11/1993 | Mehta | |
| 5,669,931 A | 9/1997 | Kupiecki et al. | |
| 5,800,549 A * | 9/1998 | Bao | A61F 2/441 606/99 |
| 6,096,022 A | 8/2000 | Laymon et al. | |
| 6,440,098 B1 * | 8/2002 | Luscher | A61B 17/0467 604/15 |
| 6,544,236 B1 * | 4/2003 | Cragg | A61B 17/0057 604/254 |
| 2001/0039455 A1 | 8/2001 | Simon et al. | |
| 2011/0009872 A1 | 1/2011 | Mistry et al. | |
| 2018/0256108 A1 | 9/2018 | Au-Yeung et al. | |

FOREIGN PATENT DOCUMENTS

WO     2004098420 A2    9/2018

OTHER PUBLICATIONS

International Search Report and Written Opinion issued in connection with International Patent Application No. PCT/US2020/024547 dated Jul. 15, 2021, 11 pages.

* cited by examiner

*Primary Examiner* — Javier G Blanco
(74) *Attorney, Agent, or Firm* — DUANE MORRIS LLP (57) ABSTRACT

A novel hydraulic implant delivery system for introducing a hydrogel implant into a cartilage repair site is disclosed.

6 Claims, 8 Drawing Sheets

HYDRAULIC IMPLANT INTRODUCER

CROSS-REFERENCE TO RELATED APPLICATIONS

This application is a National Stage Application, filed under 35 U.S.C. 371, of International Patent Application No. PCT/US2020/024547, filed on Mar. 25, 2020, which claims the benefit of U.S. patent application Ser. No. 62/878,516, filed Jul. 25, 2019, the entireties of which are incorporated herein by reference.

FIELD OF DISCLOSURE

The present disclosure relates generally to orthopedic implants, and more specifically, to an instrumentation and system for introducing a hydrogel implant into an implant site.

BACKGROUND

Hydrogel implants can be used to replace deteriorated or otherwise damaged cartilage within a joint. Such implants can be used to treat osteoarthritis, rheumatoid arthritis, other inflammatory diseases, generalized joint pain, and joint damages.

Particularly, hydrogel implants are useful in replacing deteriorated or damaged portions of cartilage within a joint with more specificity in terms of ability to repair areas of varying sizes. Advantageously, hydrogel implants having a body consisting essentially of hydrogel material that can be compressed and inserted into a receiving hole or a recess prepared in a bone being repaired results in the hydrogel implants with good stability and longevity.

A variety of types of introducer devices may be used to introduce or implant such hydrogel implants into the receiving hole in the bone. These introducer devices operate by squeezing a hydrogel implant into and through a tube-like body while holding the discharge end of the introducer device in a receiving hole or a recess in a bone until the hydrogel implant is pushed out into the recess in the bone. However, this operation exerts some amount of force on the bone as the operator pushes out the hydrogel implant through the introducer device. In situations where the repair site is located in a joint associated with relatively small bones, such as the joints in a hand (e.g. the joints between carpal bones and metacarpal bones, the joints between metacarpal bones and phalanges bones, or the joints between different phalangeal bones), the force transmitted to the bone via the operation of the introducer device can be too much to safely complete the procedure. Therefore, an improved introducer device for implanting a hydrogel implant is desired.

SUMMARY

Disclosed herein is a hydraulic implant delivery system according to an embodiment. The implant delivery system comprises, a main body extending from a first end to a second end and a channel defined therein for delivering a supply of saline solution therethrough, a nozzle removably attached to the second end of the main body, and a syringe for holding and delivering a supply of saline solution to the main body. In this embodiment, the nozzle extends away from the second end of the main body and terminates with a neck portion. The nozzle comprises a lumen extending therethrough and in fluid communication with the main body's channel. The nozzle further comprising a hydrogel implant in a compressed state pre-loaded and positioned in the lumen and the lumen forms a dispensing opening at the neck portion for dispensing the pre-loaded hydrogel implant and a nozzle input opening at the end opposite from the dispensing opening. The hydrogel implant has a leading end, a trailing end, and an exterior sidewall extending between the leading end and a trailing end. The lumen of the nozzle has a generally frusto-conical shape, whereby the dispensing opening has a smaller diameter than the nozzle input opening. The dispensing opening has a smaller diameter than the leading end of the hydrogel implant, whereby in the compressed state inside the lumen, the hydrogel implant has the same diameter as the lumen. The syringe is connected to the first end of the main body and in fluid communication with the cavity of the main body.

A hydraulic implant delivery system according to another embodiment is also disclosed. The implant delivery system comprises a main body extending from a first end to a second end and a channel defined therein for delivering a supply of saline solution therethrough, a nozzle removably attached to the second end of the main body, and a syringe for holding and delivering a supply of saline solution to the main body. In this embodiment, the nozzle extends away from the second end of the main body and terminates with a neck portion and the nozzle comprises a lumen extending therethrough and in fluid communication with the main body's channel. The lumen forms a dispensing opening at the neck portion, for dispensing a hydrogel implant that is positioned in the lumen, and a nozzle input opening at the end opposite from the dispensing opening. The lumen of the nozzle has a generally frusto-conical shape, whereby the dispensing opening has a smaller diameter than the nozzle input opening. The syringe is connected to the first end of the main body and in fluid communication with the cavity of the main body.

The hydraulic implant delivery system of the present disclosure provides an improved way to deliver hydrogel implants into a joint repair site compared to the existing implant delivery devices.

BRIEF DESCRIPTION OF THE DRAWINGS

The inventive hydraulic implant delivery system of the present disclosure will be described in more detail in conjunction with the following drawing figures. The structures in the drawing figures are illustrated schematically and are not intended to show actual dimensions.

DETAILED DESCRIPTION

This description of the exemplary embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

Figure 1:
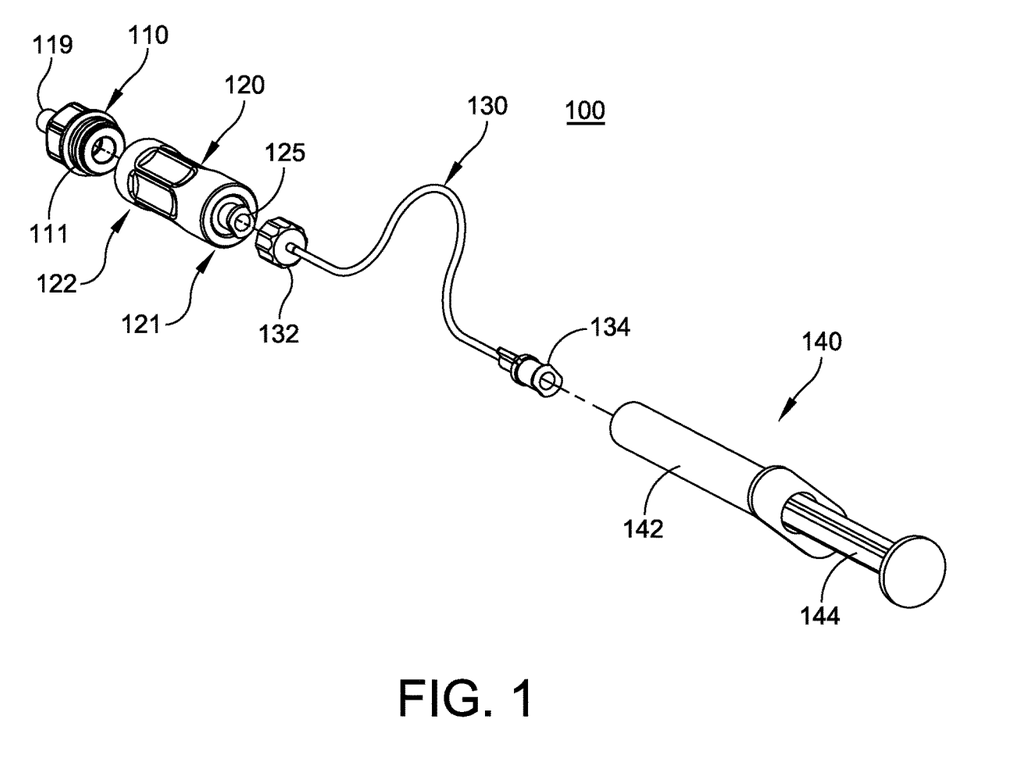
FIG. 1 is an exploded view illustration of an embodiment of the hydraulic implant delivery system according to the present disclosure.
Figure 2:
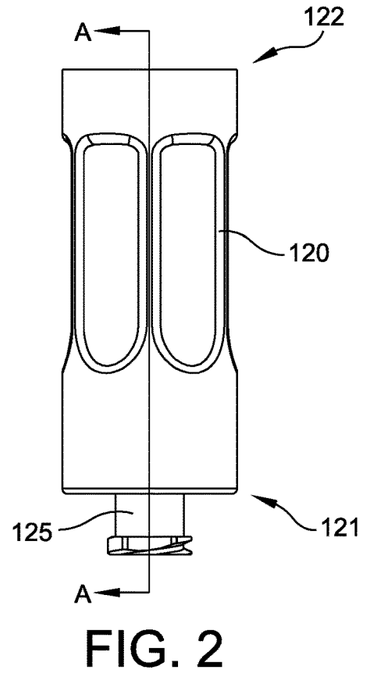
FIG. 2 is a detailed view illustration of the main body of the hydraulic implant delivery system of FIG. 1.
Figure 3:
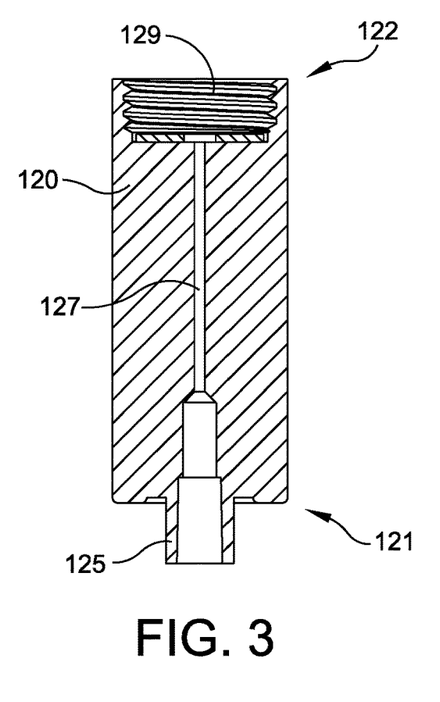
FIG. 3 is a cross-section view illustration of the main body shown in FIG. 2 taken through the section line A-A shown in FIG. 2.

Referring to FIGS. 1-3, an implant delivery system 100 according to an embodiment of the present disclosure is disclosed. The implant delivery system 100 comprises a main body 120 having a first end 121 and a second end 122. At the first end 121, a nozzle 110 pre-loaded with a hydrogel implant 500 (see FIG. 11) is removably connected to the main body 120. The first end 121 of the main body 120 is connected to a syringe 140 via a flexible tubing 130. The syringe 140 comprises a syringe body 142 and a plunger 144. The flexible tubing 130 provides a connection providing fluid communication between the syringe 140 and the main body 120 and to the nozzle 110 when the nozzle 110 is connected to the main body 120. The fluid communication allows the system to be filled with a fluid, preferably saline solution, for delivering hydraulic pressure to the hydrogel implant 500 pre-loaded in the nozzle 110 for pushing the hydrogel implant 500 out of the nozzle and into the intended joint repair site.

The main body 120 extends from a first end 121 to a second end 122. The main body 120 has a channel 127 defined therein extending through the main body's full length for delivering a supply of the saline solution therethrough. The nozzle 110 is removably attached to the second end 122 of the main body 120. As shown in FIGS. 1 and 3, the nozzle 110 is configured with a male threaded portion 111 and the main body 120 is configured with a female threaded opening 129 at its second end 122 for receiving the nozzle's threaded portion 111 for removably connecting to the nozzle 110.

The nozzle 110 extends away from the second end 122 of the main body 120 and terminates with a neck portion 119.

Referring to FIGS. 8-11, the nozzle 110 comprises a lumen 116 extending therethrough and in fluid communication with the main body's channel 127. The nozzle 110 further comprises a hydrogel implant 500 that is pre-loaded and positioned in the lumen 116. The pre-loaded configuration is shown in the cross-sectional view in FIG. 11.

Figure 10:
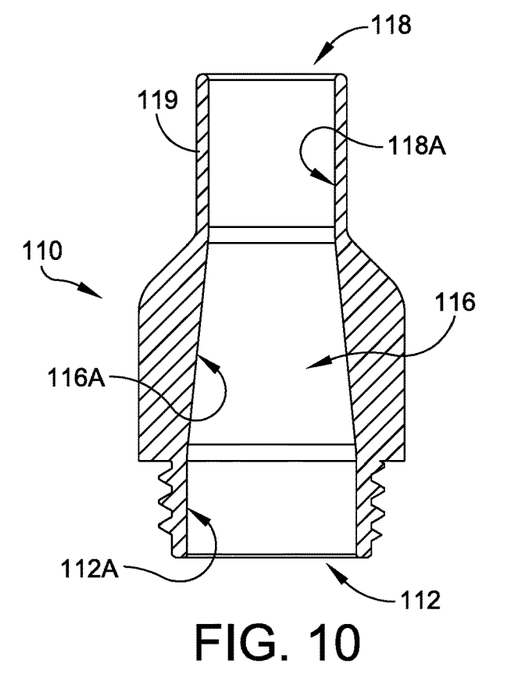
FIG. 10 is a longitudinal cross-section view illustration of the exemplary nozzle portion of the hydraulic implant delivery system shown in FIGS. 8 and 9.
Figure 11:
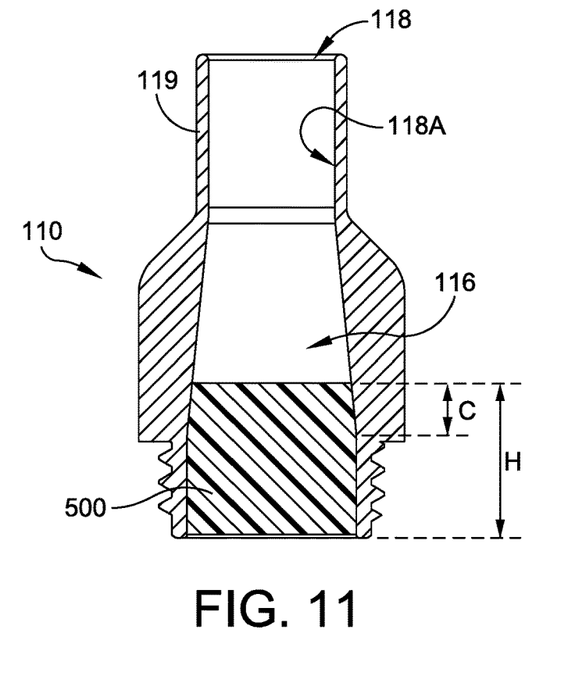
FIG. 11 is the longitudinal cross-section view of the nozzle in FIG. 10 that is pre-loaded with a hydrogel implant.

The lumen 116 extends through the full length of the nozzle 110 and forms a nozzle input opening 112 at one end through which the hydrogel implant 500 is inserted into its pre-loaded position. The lumen 116 also forms a dispensing opening 118 at the neck portion 119, which is at the end opposite from the nozzle input opening 112, for dispensing the pre-loaded hydrogel implant 500.

Figure 9A:
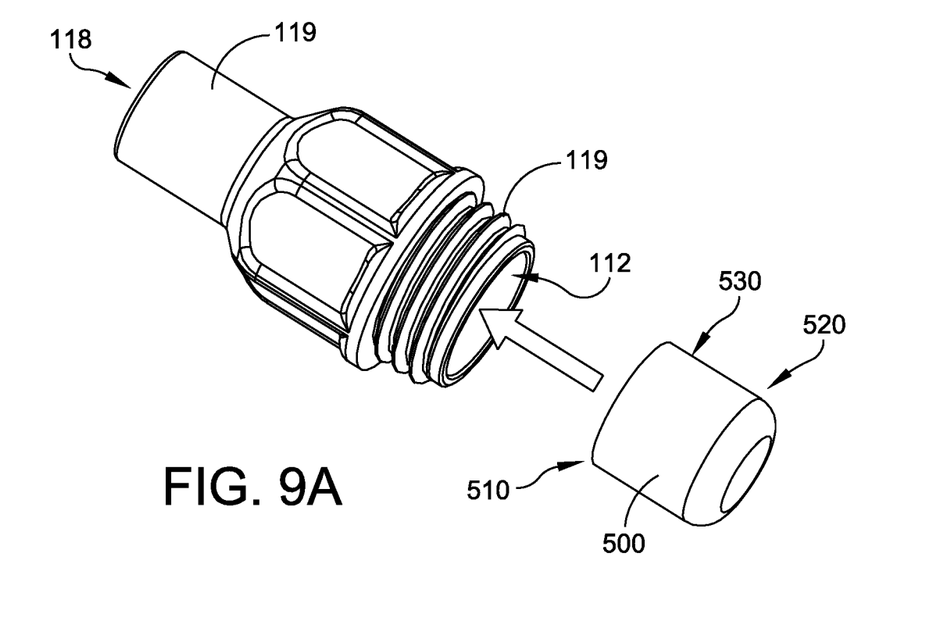
FIG. 9A is an illustration showing the orientation of a hydrogel implant being loaded into the nozzle portion of the hydraulic implant delivery system.
Figure 9B:
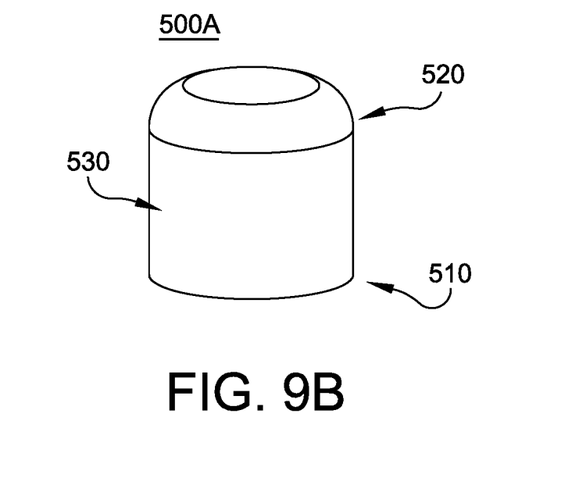
FIGS. 9B and 9C are illustrations showing the shapes of different examples of the hydrogel implant.
Figure 9C:
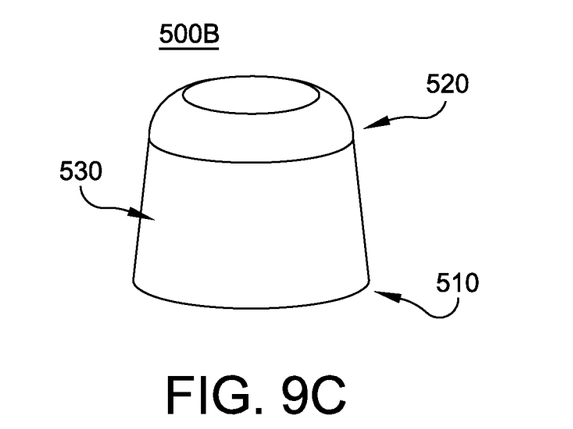

The hydrogel implant 500 used in the implant delivery system disclosed herein has a leading end 510, a trailing end 520, and an exterior sidewall 530 extending between the leading end and a trailing end. FIGS. 9B and 9C show exemplary embodiments 500A, 500B of the hydrogel implant in their uncompressed at-rest state before they are inserted into the nozzle 110. FIG. 9B shows a hydrogel implant embodiment 500A that has a cylindrical shape with the leading end 510 and the trailing end 520 having the same diameter. FIG. 9C shows a hydrogel implant embodiment 500B that has a generally frusto-conical shape with the leading end 510 having a larger diameter than the trailing end 520.

Figure 12:
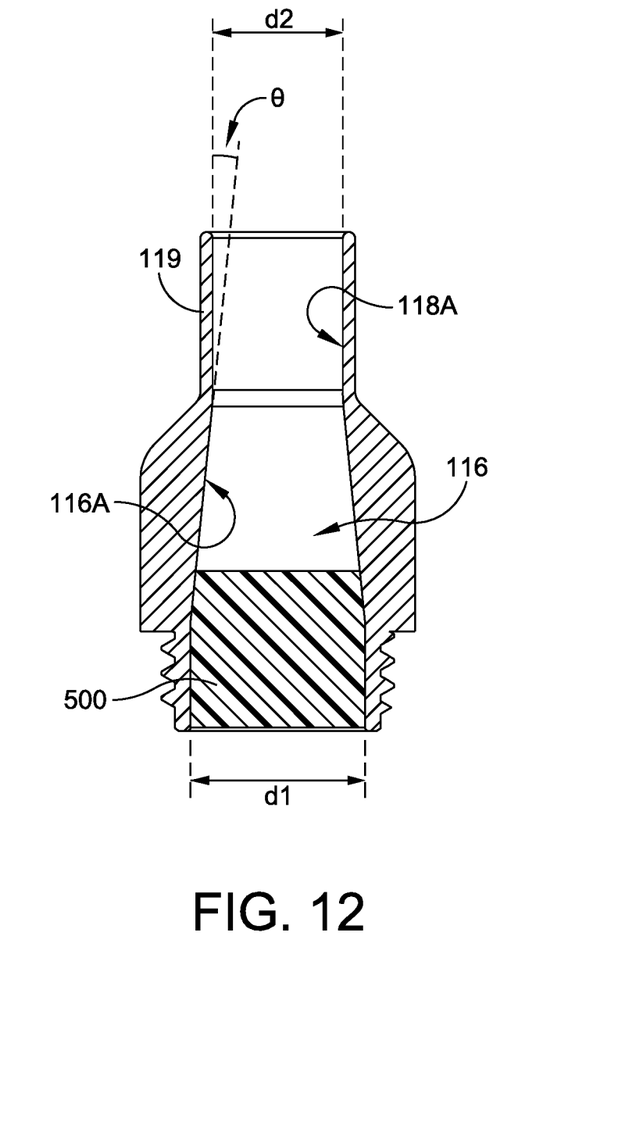
FIG. 12 is a longitudinal cross-section view of the nozzle similar to that of FIGS. 10 and 11, but identifying diameters d1 and d2.

The lumen 116 of the nozzle 110 generally comprises three main sections: the nozzle input opening 112 section formed by a first straight sidewall section 112A; the dispensing opening 118 section formed by a second straight sidewall section 118A; and a frusto-conical shaped middle portion formed by a frusto-conical shaped sidewall section 116A connecting the first straight sidewall section 112A and the second straight sidewall section 118A. The first straight sidewall section 112A has a diameter d1, and the second straight sidewall section 118A has a diameter d2, where d1 is larger than d2. The frusto-conical shaped middle portion formed by the sidewall section 116A has a generally frusto-conical shape so that the end that is connected to the first straight sidewall section 112A has the same diameter d1 as the first straight sidewall section. The end that is connected to the second straight sidewall section 118A has the same diameter d2 as the second straight sidewall section 118A, whereby the input opening 112 is larger than the dispensing opening 118.

The nozzle input opening 112 has a substantially the same diameter as the leading end 510 of the hydrogel implant 500 allowing the hydrogel implant 500 to be inserted into the nozzle input opening 112. When the hydrogel implant 500 is fully inserted into the nozzle 110 into its pre-loaded position shown in FIG. 11, the leading end 510 of the hydrogel implant extends into the frusto-conical shaped middle portion of the lumen 116 and the leading end 510 is in a compressed state. This height of the compressed portion of the hydrogel implant 500 is identified in FIG. 11 as portion C. The full height (or length depending on one's perspective) of the hydrogel implant 500 is identified in FIG. 11 as portion H. In order to accommodate cartilage repairs that require a range of different sizes of hydrogel implants, the hydrogel implant 500 can be provided in a variety of sizes in terms of its diameter and height and the nozzle 110 can be provided in a variety of sizes where the dimensions of the lumen 116 are different in each nozzle types to match the different size hydrogel implants.

For a given hydrogel material for the hydrogel implant, it becomes progressively more difficult to radially compress the implant as the size of the implant becomes smaller. In some embodiments, the hydrogel implants can be provided in 5.0 mm diameter, 6.0 mm diameter, 8.0 mm diameter, and 10.0 mm diameter. Therefore, the taper angle θ of the sidewall section 116A of the lumen 116 can be varied in order to accommodate the varying degrees of compressibility among the different sizes of the hydrogel implants 500. The taper angle θ of the sidewall section 116A can vary from about 3.98° for the 5.0 mm diameter implant to 5.71° for the 10.0 mm diameter implant. The taper angle θ of the sidewall section 116A is identified in the cross-sectional view in FIG. 12.

Additionally, the ratio of the height of the compressed portion C to the full height H of the hydrogel implant, C/H, can be adjusted along with the size of the hydrogel implant in order to account for the varying degree of compressibility mentioned above. The ratio C/H can vary from about 0.2 for the 5.0 mm diameter implant to 0.4 for the 10.4 mm diameter implant.

In the compressed state, the leading end 510 of the hydrogel implant is radially compressed and forms an intimate contact with the interior surface of the lumen 116. The quality of this intimate contact is liquid tight and prevents any liquid such as the saline solution used in the implant delivery system from passing between the hydrogel implant 500 and the interior surface of the lumen 116.

The implant delivery system 100 further comprises a syringe 140 for holding and delivering a supply of saline solution to the main body 120 and the nozzle 110 for dispensing the pre-loaded hydrogel implant 500. The syringe 140 is connected to the first end 121 of the main body 120 and is in fluid communication with the cavity 127 of the main body 120.

According to the disclosed embodiment, a flexible tubing 130 connects the syringe 140 to the first end 121 of the main body 120. In some embodiments, the flexible tubing 130 is removably connected to the syringe 140 and the first end 121 of the main body 120. The removable connections can be made by the use of Luer lock structures found in medical syringe structures. For example, the flexible tubing 130 can be configured with a female Luer lock connector 134 at the end that connects to the syringe 140 and the syringe 140 would be configured accordingly with a male Luer lock connector structure to connect to the female Luer lock connector 134. The other end of the flexible tubing 130 can be configured with a male Luer lock connector 132 and the first end 121 of the main body 120 can be configured with a corresponding female Luer lock connector 125 to connect to the flexible tubing 130.

The flexible tubing 130 can be any suitable tubing such as polymer tubing used in medical applications sufficient to withstand the static pressure generated by the saline solution while the hydrogel implant 500 is being pushed through the nozzle 110 during the implant delivery operation.

Referring to FIGS. 4-7, another embodiment of the implant delivery system 200 is disclosed. In this embodiment 200, the main body 220 which has the same structures as the main body 120 in the first embodiment 100, comprises a handle piece 228 extending from the main body 220 at an angle for allowing a user to hold the handle piece 228 and manipulate the neck portion 119 of the nozzle 110 into a desired location for dispensing the hydrogel implant 500. The desired location would be bone in a joint that has been prepared with a recess for receiving the hydrogel implant 500.

Figure 4:
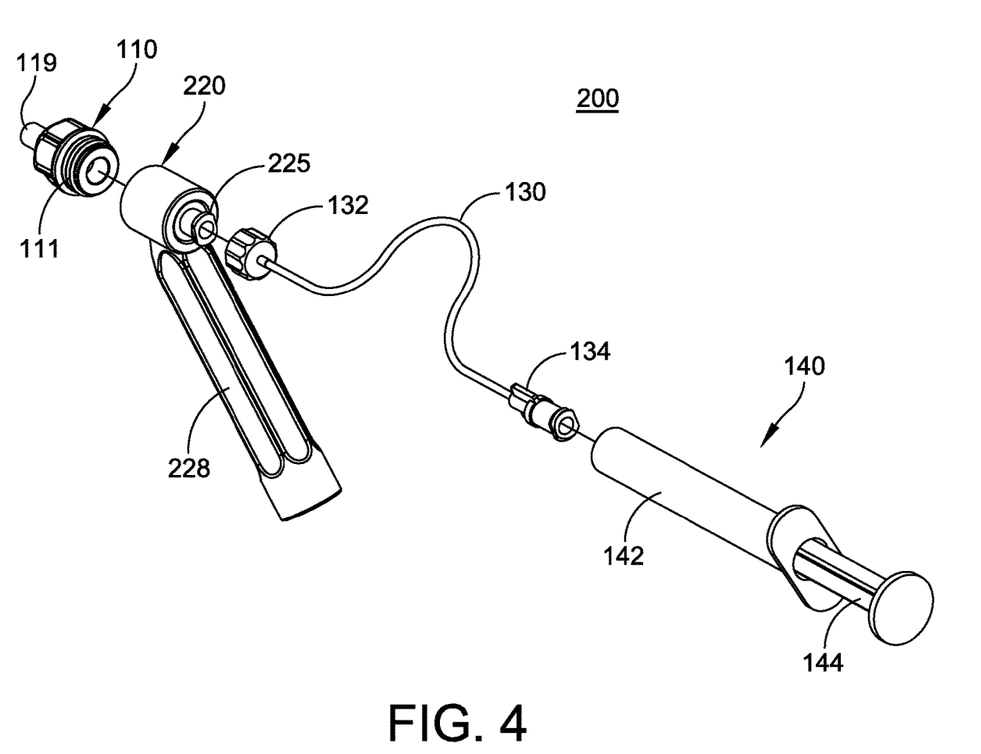
FIG. 4 is an exploded view illustration of another embodiment of the hydraulic implant delivery system according to the present disclosure.
Figure 5:
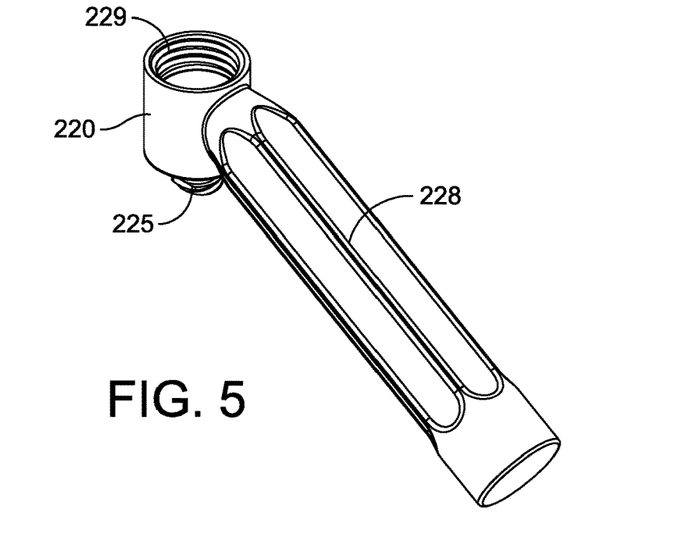
FIGS. 5 and 6 are detailed view illustration of the main body and the handle piece of the hydraulic implant delivery system of FIG. 4.
Figure 6:
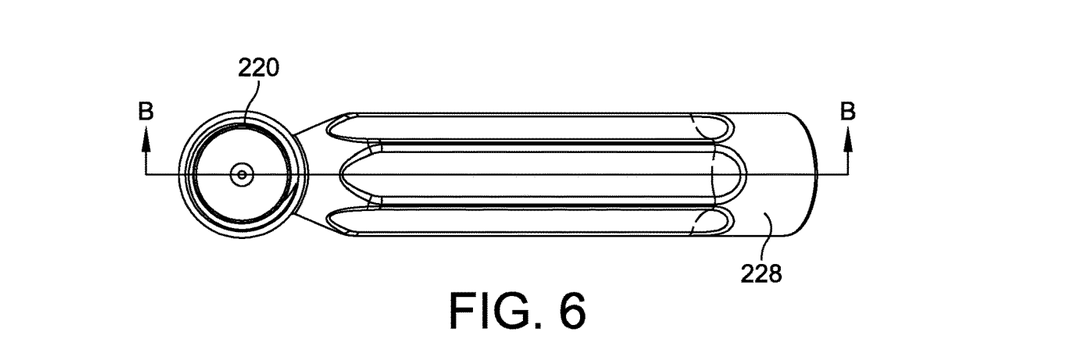
Figure 7:
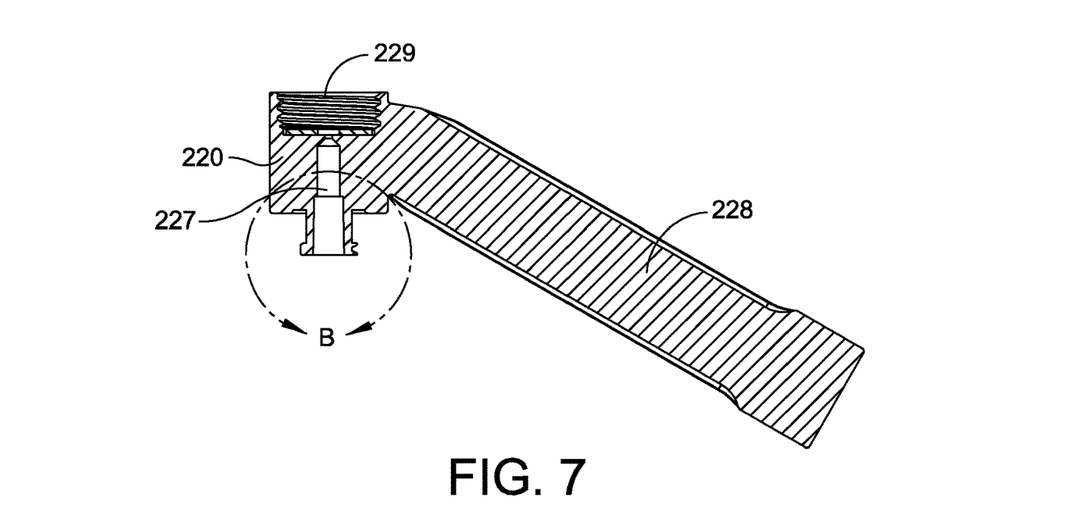
FIG. 7 is a cross-section view illustration of the structure shown in FIG. 5 taken through the section line B-B shown in FIG. 6.
Figure 8:
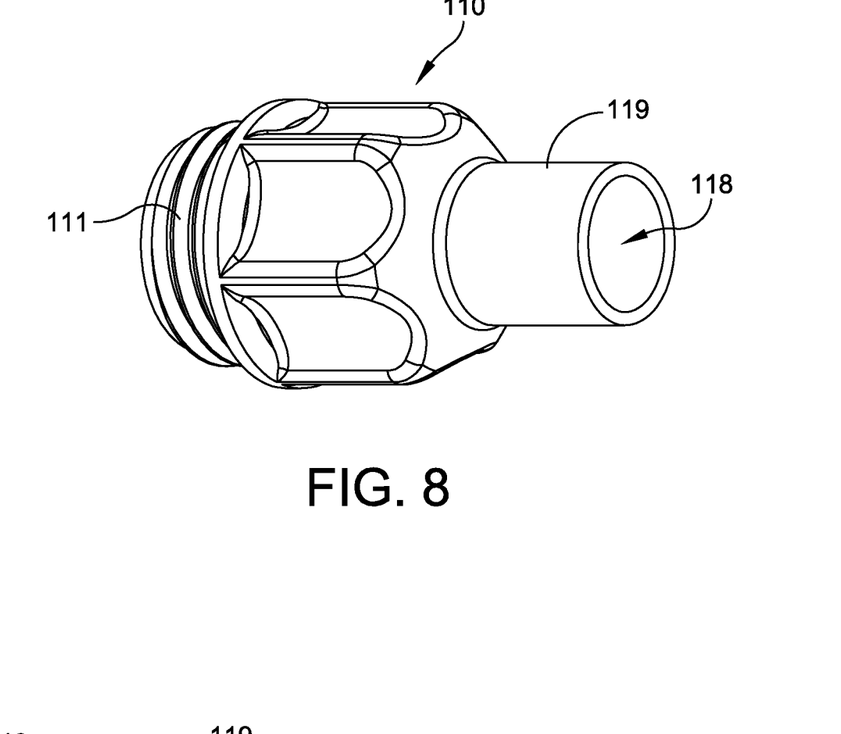
FIG. 8 is a perspective view of an example of a nozzle portion of the hydraulic implant delivery system.

As shown in FIG. 4, the main body 220 in this embodiment comprises a first end 221 and a second end 222 and is configured with a female Luer lock connector 225 at its first end 221 for removably connecting to the male Luer lock connector 132 of the flexible tubing 130. FIG. 5 shows a perspective view of the handle piece 228 and the main body 220 from the second end 222 side. FIG. 6 is another view of the main body 220 and the handle piece 228 from an angle looking directly into the second end 222 and the channel 227. FIG. 7 is a cross-sectional view of the main body 220 and the handle piece 228 taken through the section line B-B in FIG. 6. The channel 227 can be seen extending through the main body 220. The first end 221 of the main body 220 is configured with the female Luer lock connector 225. The second end 222 of the main body 220 is configured with a female threaded opening 229 for threadably connecting to the nozzle 110.

The implant delivery system 100, 200 can be pre-filled with saline solution and packaged in a sterile packaging to be provided to a surgeon in an operating room. The syringe 140, the flexible tubing 130, and the main body 120, 220 would be connected and filled with saline solution so that the surgeon just has to attach a pre-loaded nozzle 110 to the main body 120, 220 to deliver a hydrogel implant to a cartilage repair surgery site. A plurality of pre-loaded nozzles can be provided, each pre-loaded with a different size hydrogel implant. The surgeon just has to select a nozzle holding an implant of the desired size, attach the nozzle to the main body 110, 220, and operate the hydraulic implant delivery system to deliver the hydrogel implant to the cartilage repair site. The pre-loaded nozzles can be individually packaged in sterile packages or packaged in groups of desired implant sizes.

After the pre-loaded nozzle 110 is attached to the main body 120, 220, the neck portion 119 of the nozzle 110 is positioned in a previously prepared recess in a bone for receiving the hydrogel implant 500. Then, while the user is holding the main body 120, 220 in position, the plunger 144 is pressed into the syringe body 142 with sufficient force to generate enough hydraulic pressure within the implant delivery system 100, 200 for the saline solution to push the pre-loaded implant 500 through the lumen 116 of the nozzle 110 and out through the dispensing opening 118 and into the recess in the bone. Because the tapered portion of the lumen 116 and the dispensing opening 118 have smaller diameter than the hydrogel implant 500, the hydrogel implant 500 gets compressed throughout its travel through the lumen and remains in a radially-compressed state until it exits the nozzle 110 and into the recess in the bone. The recess in the bone has been prepared to have a diameter that is appropriately sized (slightly smaller than the initial diameter of the hydrogel implant) so that when the hydrogel implant 500 decompresses and tries to return to its initial diameter, a snug interference fit is created between the hydrogel implant 500 and the recess in the bone. This holds the hydrogel securely in its place.

In other examples, the hydraulic implant delivery system 100, 200 can be packaged and provided without being filled with saline solution. The surgeon would need to fill the syringe 140 with saline solution in the operating room to use the implant delivery system.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

I claim:

1. An articular cartilage implant delivery system comprising:
   a main body extending from a first end to a second end and a channel defined therein for delivering a supply of saline solution therethrough;
   a nozzle removably attached to the second end of the main body,
   wherein the nozzle is configured with a male threaded portion and the main body is configured with a female threaded opening at its second end for receiving the nozzle's threaded portion for removably attaching to the nozzle,
   wherein the nozzle extends away from the second end of the main body and terminates with a neck portion,
   wherein the nozzle comprises a lumen extending therethrough and in fluid communication with the main body's channel,
   wherein the nozzle further comprising an articular cartilage hydrogel implant in a compressed state pre-loaded and positioned in the lumen, and
   wherein the lumen of the nozzle forms a dispensing opening at the neck portion for dispensing the pre-loaded hydrogel implant and a nozzle input opening at the end opposite from the dispensing opening;
   wherein the hydrogel implant has a leading end, a trailing end, and an exterior sidewall extending between the leading end and a trailing end;
   wherein the lumen of the nozzle has a generally frusto-conical shape, whereby the dispensing opening has a smaller diameter than the nozzle input opening;
   wherein the channel of the main body has a smaller diameter than the dispensing opening of the nozzle;
   wherein the dispensing opening has a smaller diameter than the leading end of the hydrogel implant, whereby in the compressed state inside the lumen, the hydrogel implant has the same diameter as the lumen;
   a syringe for holding and delivering a supply of saline solution to the main body, wherein the syringe is connected to the first end of the main body and in fluid communication with the channel of the main body; and
   a flexible tubing connecting the syringe and the first end of the main body.

2. The implant delivery system of claim 1, wherein the flexible tubing is removably connected to the syringe and the first end of the main body.

3. The implant delivery system of claim 1, wherein the main body has a handle piece extending from the main body for allowing a user to hold the handle piece and manipulate the neck portion of the nozzle into a desired location for dispensing the hydrogel implant.

4. The implant delivery system of claim 3, wherein the handle piece extends from the main body at an angle.

5. The implant delivery system of claim 1, wherein the hydrogel implant has a generally cylindrical shape in its uncompressed state before the hydrogel implant is loaded into the nozzle.

6. The implant delivery system of claim 1, wherein the hydrogel implant has a frusto-conical shape in its uncompressed state before the hydrogel implant is loaded into the nozzle, wherein in the uncompressed state the leading end has a larger diameter than the trailing end.

* * * * *